United States Patent [19]

Nemec

[11] 4,023,574
[45] May 17, 1977

[54] ELECTROSTIMULATION METHOD AND APPARATUS

[76] Inventor: Hans Nemec, Austrasse 1, A-6830 Rankweil, Austria

[22] Filed: Oct. 20, 1975

[21] Appl. No.: 624,773

[30] Foreign Application Priority Data

Oct. 18, 1974 Austria .............................. 8407/74

[52] U.S. Cl. .............................. 128/420 A; 128/422
[51] Int. Cl.² ............................................. A61N 1/36
[58] Field of Search ........... 128/420, 420 A, 419 R, 128/421, 422

[56] References Cited

UNITED STATES PATENTS

| | | | |
|---|---|---|---|
| 2,622,601 | 12/1952 | Nemec | 128/422 |
| 3,096,768 | 7/1963 | Griffith | 128/422 |
| 3,774,620 | 11/1973 | Hansjurgens | 128/420 A |
| 3,895,639 | 7/1975 | Rodler | 128/420 A |

FOREIGN PATENTS OR APPLICATIONS 467,502   6/1937   United Kingdom ........... 128/420 A Primary Examiner—Robert W. Michell
Assistant Examiner—Lee S. Cohen
Attorney, Agent, or Firm—Ernest G. Montague; Karl F. Ross; Herbert Dubno

[57] ABSTRACT

Three separate pairs of electrodes are attached to a body part to be treated, spaced apart around said part of the body. A primary alternating electrical current having a primary frequency of between 100 Hz and 100,000 Hz is passed between one of the electrode pairs. A similar second alternating electrical current having a secondary frequency in the same range as the primary frequency but differing by between 50 Hz and 100 Hz from the primary frequency is passed between another of the pairs of electrodes. A tertiary alternating current is passed between the third pair of electrodes and has a tertiary frequency differing by at most 1 Hz from the frequency of either the primary current, the secondary current, or the arithmetic means of the frequency of these two currents.

4 Claims, 3 Drawing Figures

4,023,574

ELECTROSTIMULATION METHOD AND APPARATUS

FIELD OF THE INVENTION

The present invention relates to a method of and apparatus for treating a human or animal body. More particularly this invention concerns the electrical stimulation of internal body parts.

BACKGROUND OF THE INVENTION

In recent years electrostimulation therapy according to the so-called interference-current method has become popular, such as described in Austrian Patent No. 165,657. In accordance with this method an alternating current having a medium frequency in a range substantially between 1000 Hz and 100,000 Hz is used, modulated at a frequency of between 0 Hz and 200 Hz. Such a current is passed between two electrodes through the organ to be treated. It is also known to use two pairs of electrodes each passing a respective alternating current through the body, which currents differ from between 0 Hz and 200 Hz so that they beat or heterodyne together in the organ being treated. With such a system the regions immediately adjacent the electrodes are not traversed by enough current for any stimulation effect, but where the two separate currents cross there is an adequate stimulation.

The strength and type of organic reactions to the electrical stimuli are generally determined by the intensity and frequency of the low-frequency amplitude-modulations of the beating alternating currents. So-called vegetative processes are best stimulated by frequencies lying in the lower quarter, that is between 0 Hz and 100 Hz, of the stimulation spectrum. The higher frequencies are more advantageous for tetaniform muscle contraction, these latter being achieved at an optimal frequency of around 50 Hz. Impulse sequences below 25 Hz lead to autogenous vibrations which according to the frequency can cause tension-relieving twitching or a slow and deeply effective kneading.

It is important to note that such electrical stimulation is only effective when the stimulation intensity is varied periodically. When the intensity remains constant its effect drops off due to the accomodation effect and can even result in damage or tiring of the body part being treated. This is overcome by varying the impulses with a frequency of between approximately 0.25 Hz and 0.50 Hz.

With such arrangements it is impossible to produce frequencies which have the exact characteristic needed for proper endogenous stimulation, since the therapeutic effects are often negated by accomodation or tiring of the cells. Furthermore the effect is very limited because the use of two electrical currents which cross each other only gives a very limited, indeed two-dimensional, field of activity. Thus the ions effective to carry out the necessary stimuli all lie in relatively limited planes so that the physiologic and therapeutic effect is greatly limited.

This latter disadvantage has been at least partially overcome in systems such as described in Austrian Patent Nos. 191,082 and 203,157. At least one of the electrodes may be displaced over the person being treated so as to move the region of effectiveness around within him. Also different dosing of the electricity by means of complicated electronic control units can also change the region where the electricity is effective.

OBJECTS OF THE INVENTION

It is therefore an object of the present invention to provide an improved method of and apparatus for electrotherapy.

Another object is the provision of such a device which can be adjusted to create an exactly balanced and modulated electrical effect over a relatively large area within a person or animal to be treated.

SUMMARY OF THE INVENTION

These objects are attained according to the present invention using a system having three separate pairs of electrodes each of which is responsible for passing electrical current through the body region being treated. In accordance with the present invention two of a given alternating currents have frequencies which differ from between 0 Hz to 100 Hz so as to produce a beat frequency ideally suited for electrode treatment. The third electrical current has a frequency which varies either from that of one of the first two frequencies or from their beat frequency as arithmetic mean by a difference equal to at most 1 Hz. Thus there is produced a heterodyned and modulated overall signal which is extremely effective for internal body treatment. At the same time the use of six different electrodes at six separate and spaced-apart locations allows the thus ideally balanced current to be applied for the production of stereometric endogenous stimulation having slowly varying intensity.

With the method and apparatus according to the present invention the principle of double interference by superposition of the three different electrical currents one on top of the other allows the stimulation pulses to be ideally matched to the type of endogenous therapy being carried out. It is possible in this matter to eliminate complicated and expensive phase modulation devices, but instead to use three relatively simple adjustable oscillators each connected to a respective electrode pair.

BRIEF DESCRIPTION OF THE DRAWING

The above and other objects, features, and advantages will become more readily apparent from the following, reference being made to the accompanying drawing in which.

SPECIFIC DESCRIPTION

Figure 1:
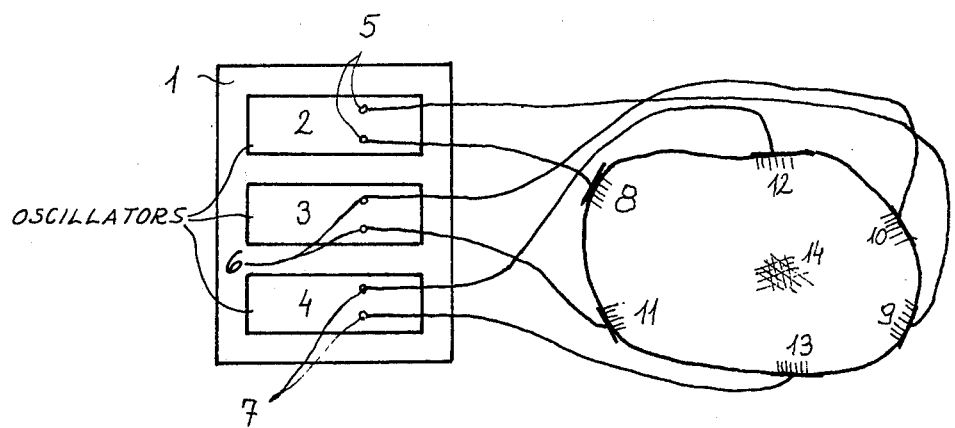
FIG. 1 is a view of the apparatus according to the present invention attached to a body part.

As shown in FIG. 1 an apparatus 1 according to the present invention is provided with three oscillators 2, 3, and 4 each having a pair of terminals 5, 6, 7 connected to respective electrode pairs 8 and 9, 10 and 11, and 12 and 13. The electrodes 8–13 are spaced around a body so as to pass respective currents $i_1$, $i_2$, $i_3$ from the oscillators 2, 3, and 4 through a given region 14 of the body.

Figure 2:
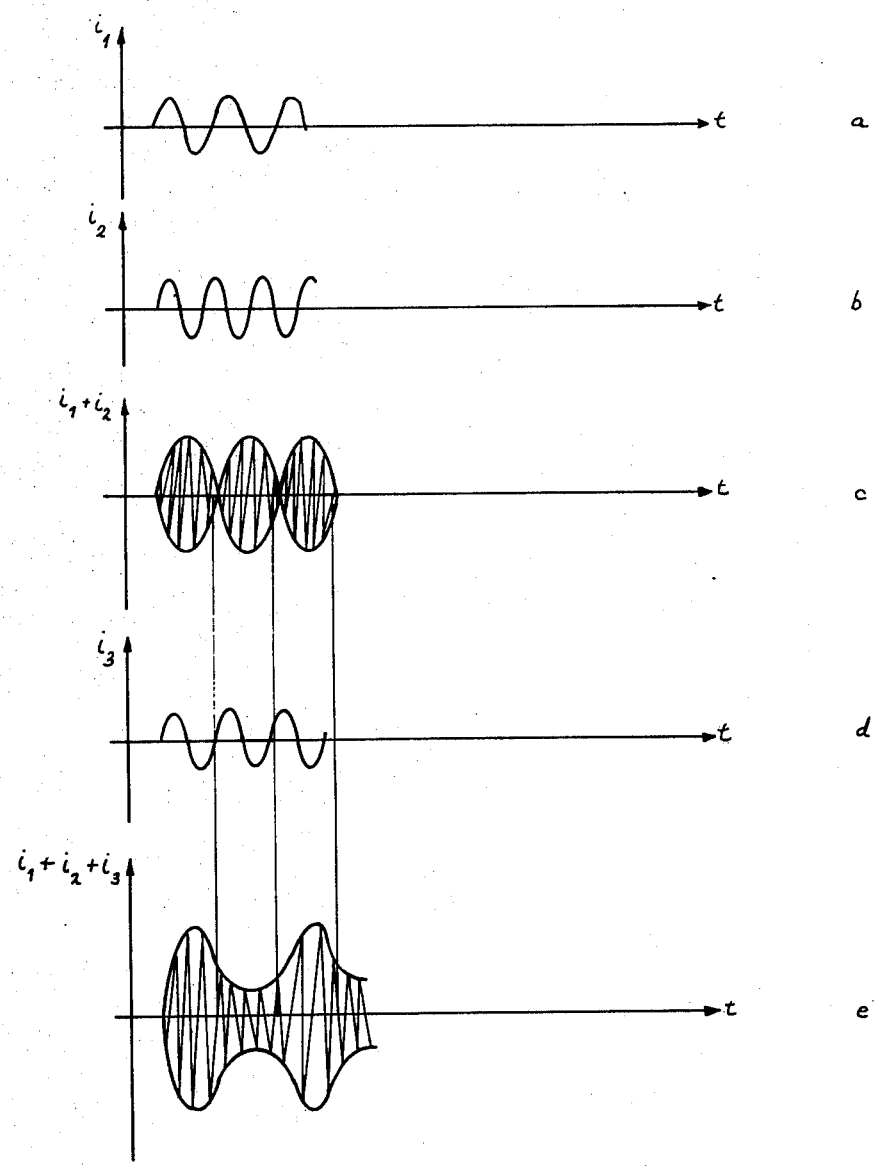
FIGS. 2 and 3 are wave diagrams illustrating functioning of the system according to this invention.
Figure 3:
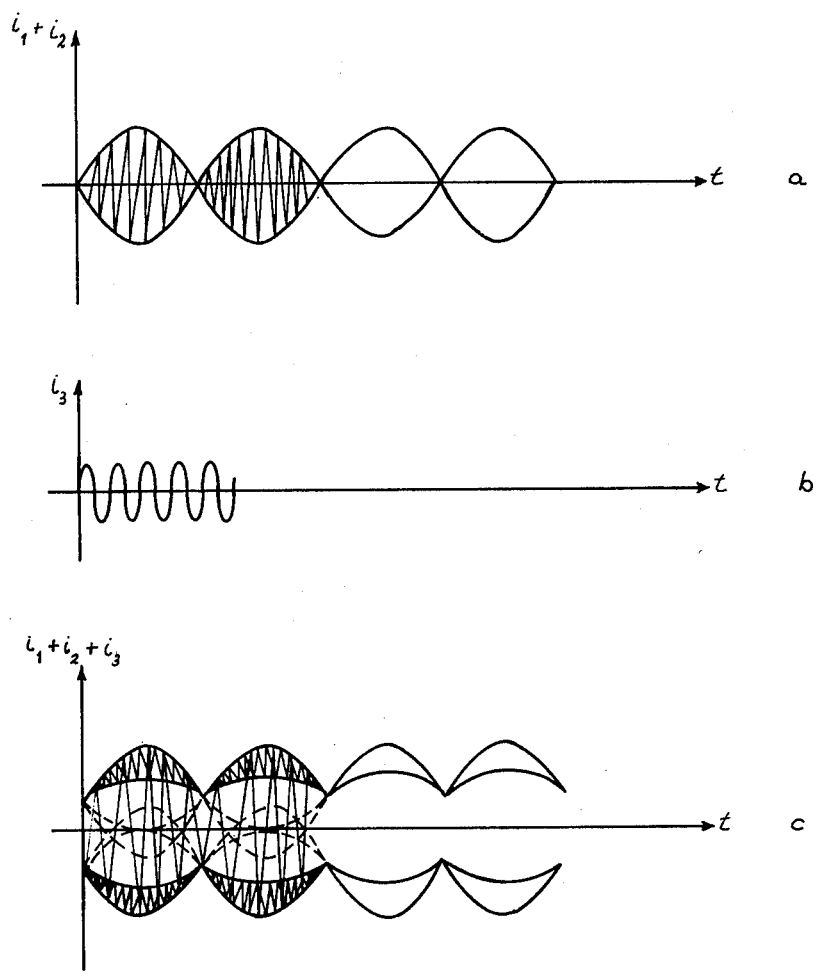

As shown in FIG. 2 at line $a$ the generator 2 produces a constant-frequency alternating signal having a frequency of 4000 Hz and constant amplitude. The other oscillator 3 has an output as shown at line $b$ in FIG. 2 which is of constant amplitude and a constant frequency of 4100 Hz. These two signals beat together as shown at line $c$ to form a modulated signal $i_1 + i_2$ beating at 100Hz. Line $d$ in FIG. 2 shows how the oscillator 4 produces an output signal $i_3$ of constant amplitude and having a frequency slightly greater than 4099 Hz. When this signal $i_3$ beats with the signal shown on line $c$ a combined signal $i_1 + i_2 + i_3$ as shown in FIG. 2 at line $e$ is produced. FIG. 3 shows another system for combining the signals.

In the treatment of paresis the optimal tetanizing stimuli have a frequency of 50 Hz. At this frequency the deep-lying motor nerve fibers and the corresponding muscles are stimulated in an optimum manner. It is also necessary for such stimulation that the stimulation pulses be varied slowly so as to prevent fatigue or accomodation in the region 14.

This effect is achieved by setting one of the generators at 4100 Hz with constant amplitude. The other generator is set in the range of 4050 Hz so as to produce the desired slow contraction rhythm. A so-called double interference effect is obtained by heterodyning the two signals with 4000 Hz and 4100 Hz so as to produce a 100 Hz amplitude modulated signal with a carrier frequency of 4050 Hz and a third current of approximately 4050 Hz with constant amplitude. Thus there is produced a slow change between the stimulation frequencies of 100 and 50 Hz, with an increase in intensity at 50 Hz. Since the stimulation effect is greater at 50 Hz than at 100 Hz, a correspondingly improved stimulation is achieved.

For the treatment of painful rheumatic afflictions, circulation difficulties, and the like the endogenous deep effect of oscillations in the so-called vegetal spectrum between 8 Hz and 25 Hz has been shown to be highly effective, particularly in treating the autonomous nervous system. Variation of the rhythm must be employed in order to prevent the system from accomodating to the stimulation. Thus a wobbulating generator is used varying between 4008 Hz and 4025 Hz for the primary stimulation current. The secondary frequency will lie above 4000 Hz and the tertiary will lie also above 4000 Hz and be less than 1 Hz different from the secondary signal to give the desired vegetative rhythm.

Preferably a primary frequency of 1,000 to 100,000 Hz and a secondary frequency of 1,000 to 100,000 Hz are used.

I claim:

1. A method of treating a human or animal body comprising the steps of:

passing between two separate primary locations through a given portion of said body a primary alternating electrical current having a primary frequency of between 1000 Hz and 100,000 Hz;

passing between two secondary locations spaced on said body from said primary locations a second alternating electrical current through said portion, said secondary current having a secondary frequency differing from said primary frequency by at most 100Hz, whereby said primary current and said secondary current may beat together at a beat frequency; and passing between two separate tertiary locations spaced on said body from said primary and secondary locations and through said portion a tertiary alternating current having a tertiary frequency differing from one of said primary, secondary and beat frequencies by at most 1 Hz.

2. The method defined in claim 1 wherein said primary frequency lies between 3950 Hz and 4050 Hz and said secondary frequency is between 50 Hz and 100 Hz greater than said primary frequency.

3. An apparatus for treating a human or animal body, said apparatus comprising:

independent primary, secondary, and tertiary pairs of electrodes, each electrode being applicable to a separate body location with said pairs of electrodes spanning a given body portion;

oscillator means for passing a primary alternating current having a primary frequency of between 1000 Hz and 100,000 Hz between said electrodes of said primary pair through said portion;

oscillator means for passing a secondary alternating electrical current having a secondary frequency differing from said primary frequency by at most 100Hz between said electrodes of said secondary pair through said portion; and oscillator means for passing through said portion between said electrodes of said tertiary pair a tertiary alternating current having a tertiary frequency differing by at most 1 Hz from said primary frequency, from said secondary frequency, or from the arithmetic mean of said primary and secondary frequencies. .

4. The apparatus defined in claim 3 wherein said secondary frequency varies between 50 Hz and 100 Hz from said primary frequency.

* * * * *